United States Patent
Cavallaro et al.

(10) Patent No.: US 6,860,156 B1
(45) Date of Patent: Mar. 1, 2005

(54) COMBINED IN-PLANE SHEAR AND MULTI-AXIAL TENSION OR COMPRESSION TESTING APPARATUS

(75) Inventors: Paul V. Cavallaro, Raynham, MA (US); Claudia J. Quigley, Lexington, MA (US); Ali M. Sadegh, Franklin Lakes, NJ (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/851,748

(22) Filed: May 24, 2004

(51) Int. Cl.[7] .................................................. G01N 3/08
(52) U.S. Cl. ............................. 73/819; 73/813; 73/818
(58) Field of Search .................... 73/813–848, 788–800, 73/760, 159, 160

(56) References Cited

U.S. PATENT DOCUMENTS

| | | | |
|---|---|---|---|
| 1,496,803 A | 6/1924 | Amsler | |
| 3,776,028 A | 12/1973 | Lynch et al. | |
| 4,192,194 A | 3/1980 | Holt | |
| 4,677,854 A | 7/1987 | Gabelli | |
| 4,885,941 A | 12/1989 | Vardoulakis et al. | |
| 5,144,844 A | 9/1992 | Mathiak et al. | |
| 5,279,166 A | 1/1994 | Ward et al. | |
| 5,448,918 A | 9/1995 | Tucchio | |
| 5,798,463 A | 8/1998 | Doudican et al. | |
| 5,905,205 A | 5/1999 | Clay | |
| 6,058,784 A | 5/2000 | Carroll et al. | |
| 6,065,330 A | * | 5/2000 | Freeman et al. ........... 73/54.28 |
| 6,085,584 A | * | 7/2000 | Ramachandran et al. ..... 73/159 |
| 6,094,259 A | * | 7/2000 | Kamegawa .................. 73/800 |
| 6,487,902 B1 | 12/2002 | Ghosh | |

OTHER PUBLICATIONS

W. Denney Freeston Jr. et al., Mechanics of Elastic Performance of Textile Materials, Part XVIII. Stress–Strain Response of Fabrics Under Two–Dimensional Loading, Manuscript, Nov. 1967, pp. 948–975, Textile Research Journal, USA.

* cited by examiner

Primary Examiner—Edward Lefkowitz
Assistant Examiner—Alandra Ellington
(74) Attorney, Agent, or Firm—James M. Kasischke; Michael P. Stanley; Jean-Paul A. Nasser

(57) ABSTRACT

An in-plane shear and multi-axial tension or compression testing apparatus having four-bar linkages pivotable to two sleeves on an opposite vertices with the sleeves of each vertex rotationally attached to each other. Lateral links of each linkage are pivotally attached to load transfer plates in which the plates secure a test specimen. Each linkage is rotatable to the other linkages while the vertices are subjected to a compression or tensile load. The vertices are also capable of rotation by a testing machine for shear testing. During compression or tension of the vertices of the apparatus, the plates respectfully move toward or away from each other thereby applying compression or tension to the specimen. The bars of one linkage can be rotated with respect to the other, thereby applying torsional loading to the specimen.

20 Claims, 10 Drawing Sheets

COMBINED IN-PLANE SHEAR AND MULTI-AXIAL TENSION OR COMPRESSION TESTING APPARATUS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION (1) Field of the Invention

The present invention relates to a combined in-plane shear loading and multi-axial tension or compression testing apparatus in which the apparatus is capable of determining the mechanical properties of metals, plastics, woods, fabrics, elastomers and other materials.

(2) Description of the Prior Art

Plain-woven fabrics are widely utilized as structural materials in air-inflated structures and rapidly deployable structures such as temporary shelters, tents, temporary bridges and space structures. Unlike metallic structures, these structures are primarily designed to be lightweight, self-erecting and deployable to volume-storage ratios that may be 1000-to-1. Air-inflated structures utilize pressurized fabric tubes and pressure-stabilized beams (known as air beams) as load-carrying members.

Although, the structures are well-known in the art, the technology for the structures has not been refined such that reliable structures can be analytically designed. Specifically, this analysis has gained in importance due to advancements in the material of the structural fiber and the weaving/braiding of the structural fiber, both of which have improved the load carrying capacity of the structures. Accordingly, there is a recognized need to model the mechanical properties of woven fabrics.

Presently, modeling the mechanical properties of woven fabrics results in complex responses because of the complex microstructures of the composite materials used. Unlike traditional composite materials, plain-woven fabrics used in inflated structures exhibit high non-linearity with a dependence on internal pressure and contact interactions within the woven fabric.

Accordingly, there is a need for a testing apparatus which measures the elastic and shear moduli of air beams as a function of inflation pressure. To measure the elastic modulus of the fabric, a multi-axial loading has been shown to be preferable and to measure the shear moduli of the fabric; an in-plane shear loading has been shown to be preferable. As such, there is a need for a testing apparatus capable of combining in-plane shear and multi-axial loading. For non-orthogonal composite or fabric materials, such as braids or knits, there is a further need for a testing apparatus capable of loading the specimen in varying non-orthogonal positions.

While biaxial testing apparatuses with compression and tension loading or in-plane shear testing apparatuses exist in the prior art, there are no apparatuses that exist with a combined feature of in-plane shear and compression/testing capabilities. Also, a testing apparatus does not exist that is capable of applying non-orthogonal multi-axial loading.

Additionally, testing apparatuses of the prior art employ two or more separate actuators in complex test fixtures or pressurization techniques for applying a biaxial load to a test specimen. An apparent disadvantage is the need for two or more loading devices and the associated high cost of equipment.

In regard to specific references, Lynch et al. (U.S. Pat. No. 3,776,028) describes an apparatus requiring three independent loading mechanisms. Holt (U.S. Pat. No. 4,192,194) describes an apparatus for biaxial loading of a specimen by pressurizing the inside surface of a cylinder. A restrictive disadvantage of the apparatus is the requirement of the cylindrical shape of the specimen and a high cost associated with pressurization of the cylinder. Additionally, the disadvantages include restriction to orthogonal loads about the axial, hoop and radial directions and an apparatus that is not capable of applying an in-plane shear stress to the specimen.

Mathiak et al. (U.S. Pat. No. 5,144,844) describes a cruciform planar specimen for biaxial material testing which has the disadvantage of being limited to use in two loading directions. Ward et al. (U.S. Pat. No. 5,279,166) describes an apparatus for self-alignment of a biaxial loading device. The apparatus requires that the two axial loading directions be orthogonal with a maximum of two loading directions. The apparatus also has no capability for applying an in-plane shear load to the specimen.

Tucchio (U.S. Pat. No. 5,448,918) describes an apparatus with an X-shape that is only used for compression load. Clay (U.S. Pat. No. 5,905,205) describes an in-plane biaxial test apparatus comprising linkages to transfer the load to an orthogonal direction of loading. A disadvantage of this apparatus is that it is not capable of applying in-plane shear to the test specimen. Another disadvantage of this apparatus is that the biaxial loading is limited to an orthogonal configuration.

As noted above, none of the references are capable of combining the in-plane and compression/tension loading of a specimen while only using one loading system. As such, there exists a need for an apparatus capable of applying a combined in-plane shear and tension/compression load to a specimen. Such an apparatus would be cost-effective due to reduced space and a reduced amount of equipment normally needed for material testing.

SUMMARY OF THE INVENTION

Accordingly, it is a general purpose and primary object of the present invention to provide an apparatus for testing a specimen with a multi-axial in-plane tension or compression loading.

A further object of the present invention is to provide an apparatus for applying a non-orthogonal multi-axial tension or compression loading to the specimen.

A still further object of the present invention is to provide an apparatus for applying in-plane shear loading to the specimen when the specimen is subjected to multi-axial loading.

A still further object of the present invention is to provide an apparatus for employing a loading system compatible with conventional prime mover testing equipment.

A still further object of the present invention is to provide an apparatus for applying an unequal and multi-axial loading to the specimen.

To attain the objects described, there is provided an apparatus for simultaneous or independent in-plane shear and tension or compression loading of a test specimen such as metals, plastics, composites, woods, fabrics or anisotropic materials. The loading of the test specimen can orthogonal or non-orthogonal.

With the apparatus, the uniaxial tensile or compressive 11 load of a test machine can be converted to an equal or unequal stress state on a planar test specimen and an orthogonal or an oblique (non-orthogonal) stress state on the specimen by the use of load transfer systems comprising four-bar linkages movable to define the borders of varying rhombus-shapes.

The apparatus also provides flexibility by the ability to apply an unequal stress state or multi-axial load to the test specimen by utilizing load transfer plates of different lengths. Additionally, the apparatus provides flexibility by the ability to apply a non-orthogonal multi-axial loading by utilizing a different angle, other than exact angles between the vertices of the four-bar linkages. The angle of rotation of the linkages between the vertices can be measured directly by the test machine through load cells or other conventional instrumentation.

More specifically in structure, the apparatus comprises two four-bar linkages for biaxial testing and capable of the addition of other four-bar linkages for testing along additional axes. The four-bar linkages defining a rhombus-shape are pivotally connected to one another at opposing ends or vertices by sleeve bearings positioned at each vertex. The sleeve bearings at each vertex are axially connected to one another with a pin and thrust bearings between the sleeve bearings 11 thereby allowing the sleeve bearings to rotate freely with respect to one another while connected in the axial (vertical direction). Load transfer plates are pivotally attached to lateral links for each of the four-bar linkages. A securing clamp for the specimen is attached to the distal end of each of the load transfer plates.

When testing a specimen, an exposed end (two ends for uniaxial loading, four ends for biaxial loading, six ends for triaxial loading etc.) of the specimen is rigidly secured by the clamp. The vertices of the apparatus are attached to the crossheads of a conventional uniaxial tensile/torsion machine. Upon a movement of the vertices of the linkages toward each other, their lateral links will extend outward thereby increasing the distance between the corresponding load transfer plates of each linkage. This movement applies planar tension on the specimen. Additionally, by rotating one linkage with respect to the other, the specimen will be subjected to the in-plane shear.

Similarly, upon movement of the vertices of the two linkages away from each other, their lateral links contract inward; thereby, decreasing the distance between the corresponding load transfer plates of each linkage. This movement applies planar compression on the specimen. Additionally, by rotating one linkage with respect to the other, the specimen will be subjected to the in-plane shear.

An added feature of the invention would be affixing a camera or optical recording device to a vertex of the apparatus. Another added feature would be the affixing a draping or puncturing mechanism to a vertex of the apparatus to conduct drape and/or puncture tests on the specimen.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings wherein.

DESCRIPTION OF THE PREFERRED EMBODIMENT

Figure 1:
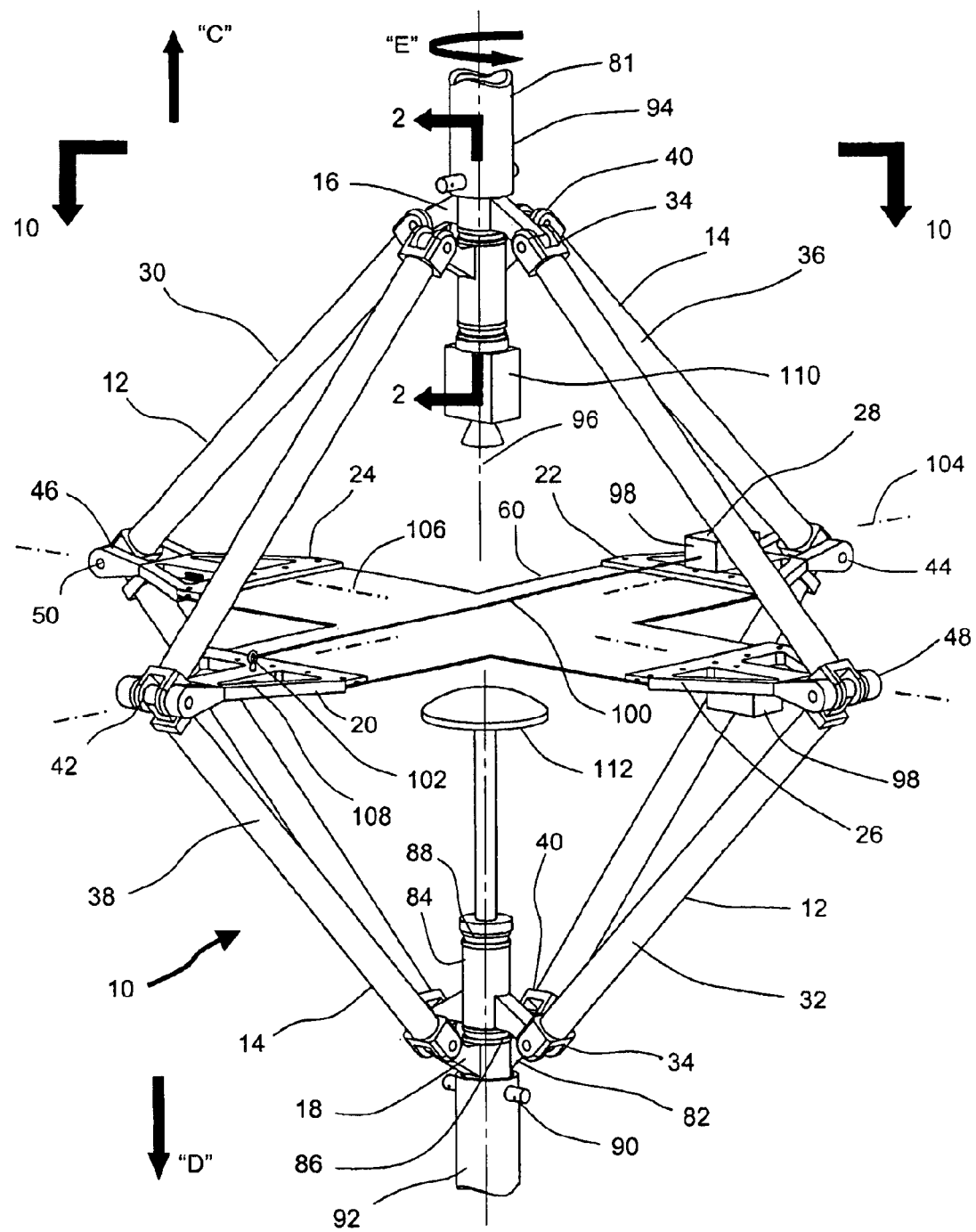
FIG. 1 depicts a perspective view of the multi-axial testing apparatus of the present invention with a specimen secured by the apparatus such that the specimen is subjected to multi-axial tension.

Referring now to the drawings wherein like numerals refer to like elements throughout the several views, one sees that FIG. 1 depicts a preferred embodiment of a testing apparatus 10 of the present invention. As shown in the figure, the apparatus 10 for biaxial loading generally comprises four-bar linkages 12 and 14 defining a perimeter of a variable rhombus shape, a first (or as shown) a top joint assembly 16, a second (or as shown) a bottom joint assembly 18, load transfer plates 20, 22, 24 and 26 and an associated strain and displacement measurement system 28.

The linkage 12 includes two pairs of oblong and rigid members 30 and 32. Each end of each member is rigidly connected to a bracket 34 in which each bracket is pivotally connected to the top joint assembly 16 and the bottom joint assembly 18. The linkage 14 includes two pairs of oblong and long rigid members 36 and 38. Each end of each member is rigidly connected to a bracket 40 in which each bracket is pivotally connected to the top joint assembly 16 and the bottom joint assembly 18.

Each of the load transfer plates 20, 22, 24 and 26, is pivotally connected to lateral links 42, 44, 46 and 48 of the linkages 12 and 14 and each secured by a pin 50. Each load transfer plate 20, 22, 24 and 26 includes a clamp of a type known to those skilled in the art, either a clamp with a first wedge 52 for tensile loading (described further below), a clamp with a second wedge 54 for compressive loading (described further below), a clamp with a tongue and groove 56 for loading of fabric or similarly flexible materials (described further below) or a clamp 58 with a pre-tensioning roller 59 for loading 11 of fabric or similarly flexible materials (described further below). Each of the clamps secures a test specimen 60 by clamping or attaching to an exposed side of the specimen.

Figure 2:
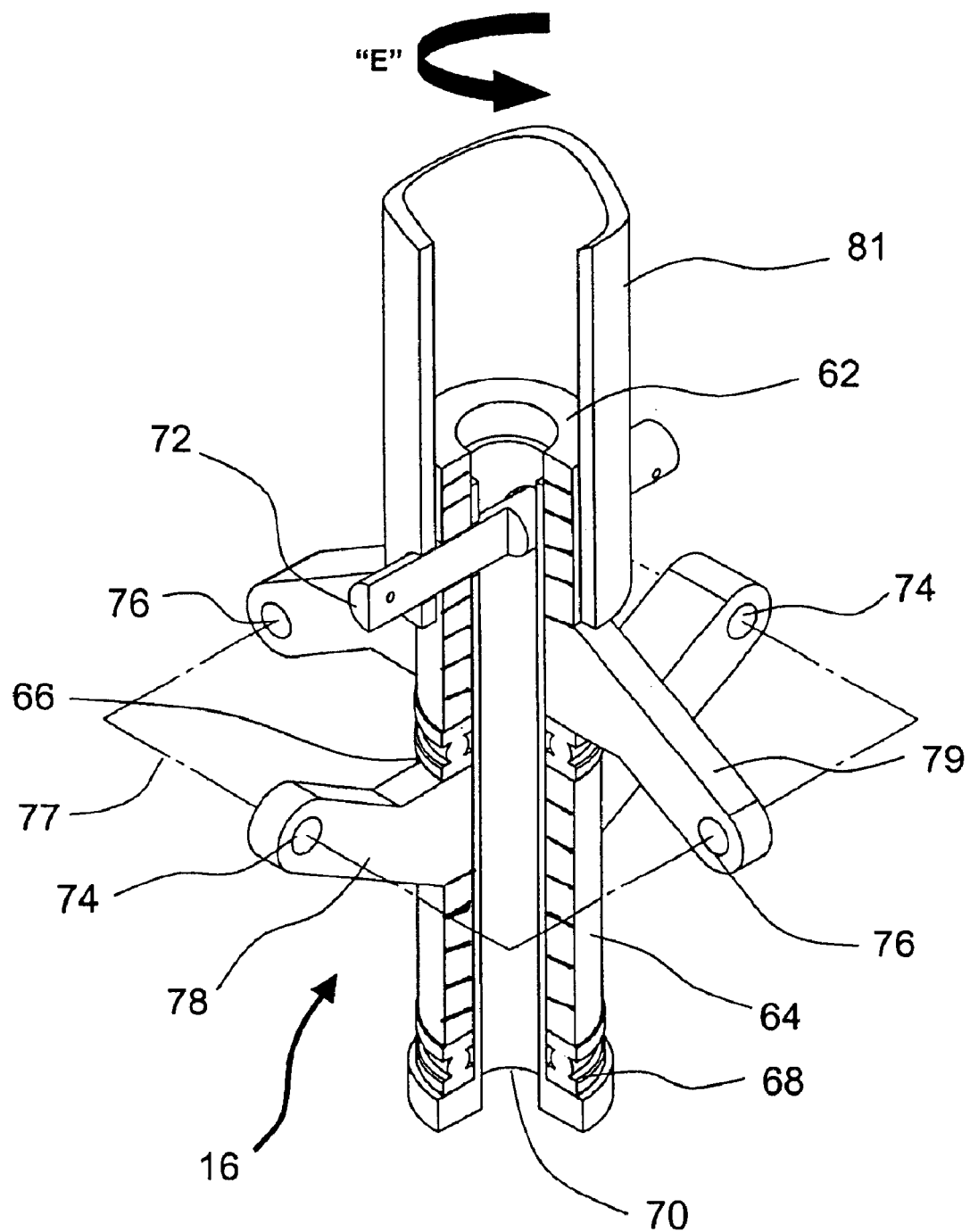
FIG. 2 depicts a cross-sectional view of a joint assembly of the apparatus of the present invention with the view taken from reference line 2—2 of FIG. 1.
Figure 3:
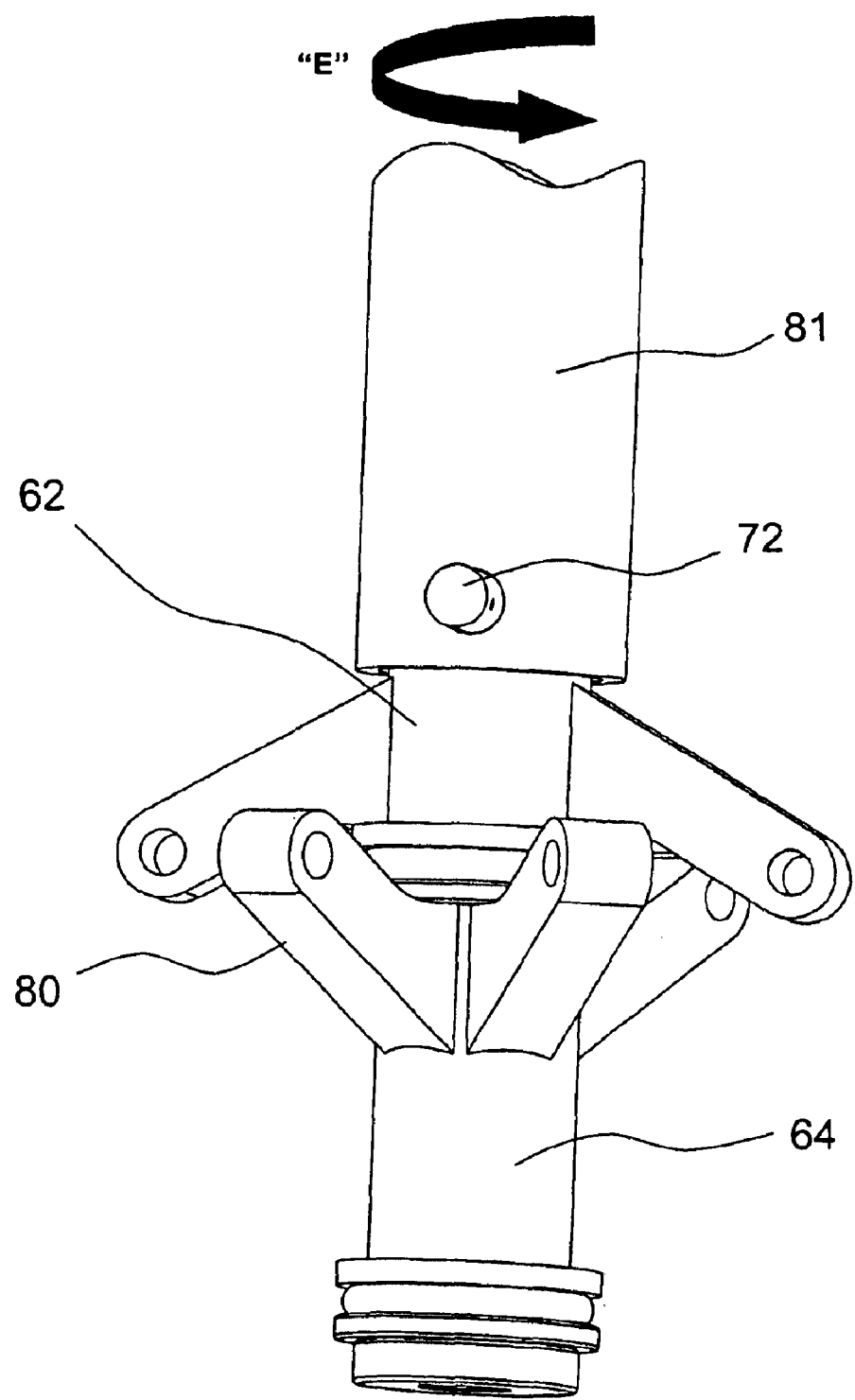
FIG. 3 depicts a view of the joint assembly of the apparatus of the present invention with an additional set of extending arms for a third linkage in support of tri-axial loading.

Referring now to the cross-sectional view of FIG. 2, the top joint assembly 16 comprises a first sleeve 62 and a second sleeve 64, a first thrust bearing 66, a second thrust bearing 68, a connecting rod 70 and a pin 72. The second sleeve 64 includes apertures 74 at the distal end of its extending arms as pivoting connecting points for the rigid members 36. Similarly, the first sleeve 62 includes apertures 76 at the distal end of its extending arms as pivoting connecting points for the rigid members 30. During loading for a test, the height of the apertures 74 and 76 of the top joint assembly 16 are on a horizontal plane 77 in which the horizontal plane is allowed by the second sleeve 64 having upward extending arms 78 and the first sleeve 62 having downward extending arms 79. As shown in FIG. 3, an additional pair of extending arms 80 are positioned on the second sleeve 64 to support a third four-bar linkage (not shown) in which tri-axial loading can be accomplished by load transfer plates of the third four-bar linkage. In this manner, additional linkages can be added to the second sleeve 64 for further multi-axial loading.

For the configurations of both figures, the pin 72 restrains the vertical motion of the sleeves 62 and 64, yet allows rotation of one sleeve with respect to the other. A crosshead 81 of a testing machine (not shown) is rigidly connected to the top joint assembly 16 by the pin 72.

Referring again to FIG. 1, the bottom joint assembly 18 is similar to the top joint assembly with the bottom joint assembly comprising a first sleeve 82, a second sleeve 84, a first thrust bearing 86, a second thrust bearing 88 and a pin 90. An additional pair of extending arms can be positioned on the first sleeve 82, similar to the positioning of extending arms 80 to support the other end of the third four-bar linkage. In this manner, additional linkages can be added to the first sleeve 82 for further multi-axial loading.

Similar to the top joint assembly 16, the vertical motion of the sleeves 82 and 84 is restricted by a pin 90, yet the sleeves rotate with respect to the other. A crosshead 92 of a testing machine (not shown) is rigidly connected to the bottom joint assembly 18 by the pin 90.

Figure 4:
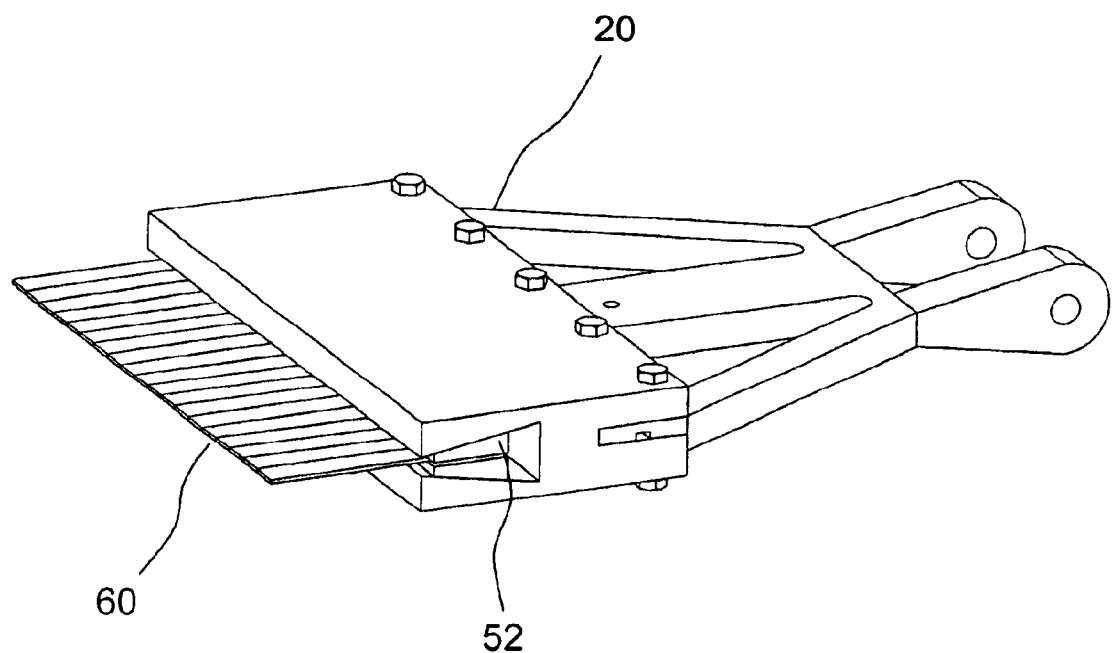
FIG. 4 depicts a tensile wedge clamp attached to a load transfer plate of FIG. 1.
Figure 5:
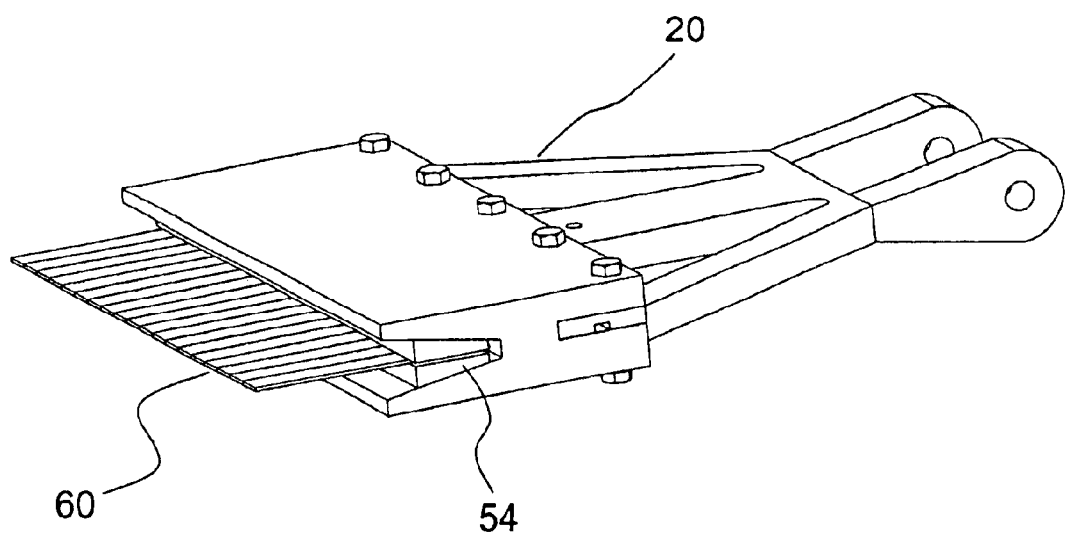
FIG. 5 depicts a compressive wedge clamp attached to the load transfer plate of FIG. 1.
Figure 6:
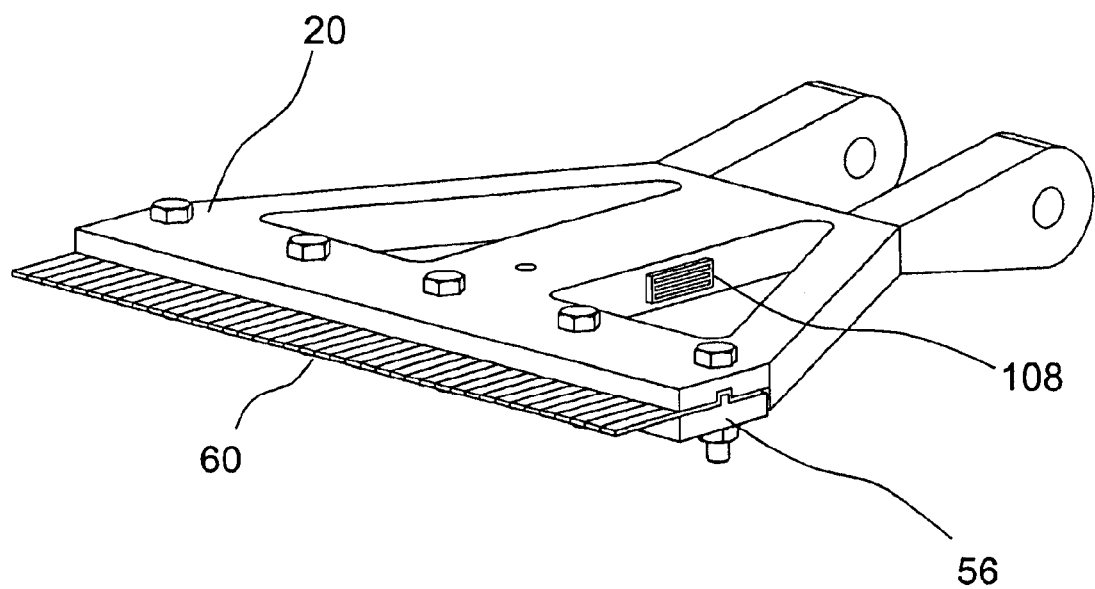
FIG. 6 depicts a tongue-and-groove clamp attached to the load transfer plate of FIG. 1.
Figure 7:
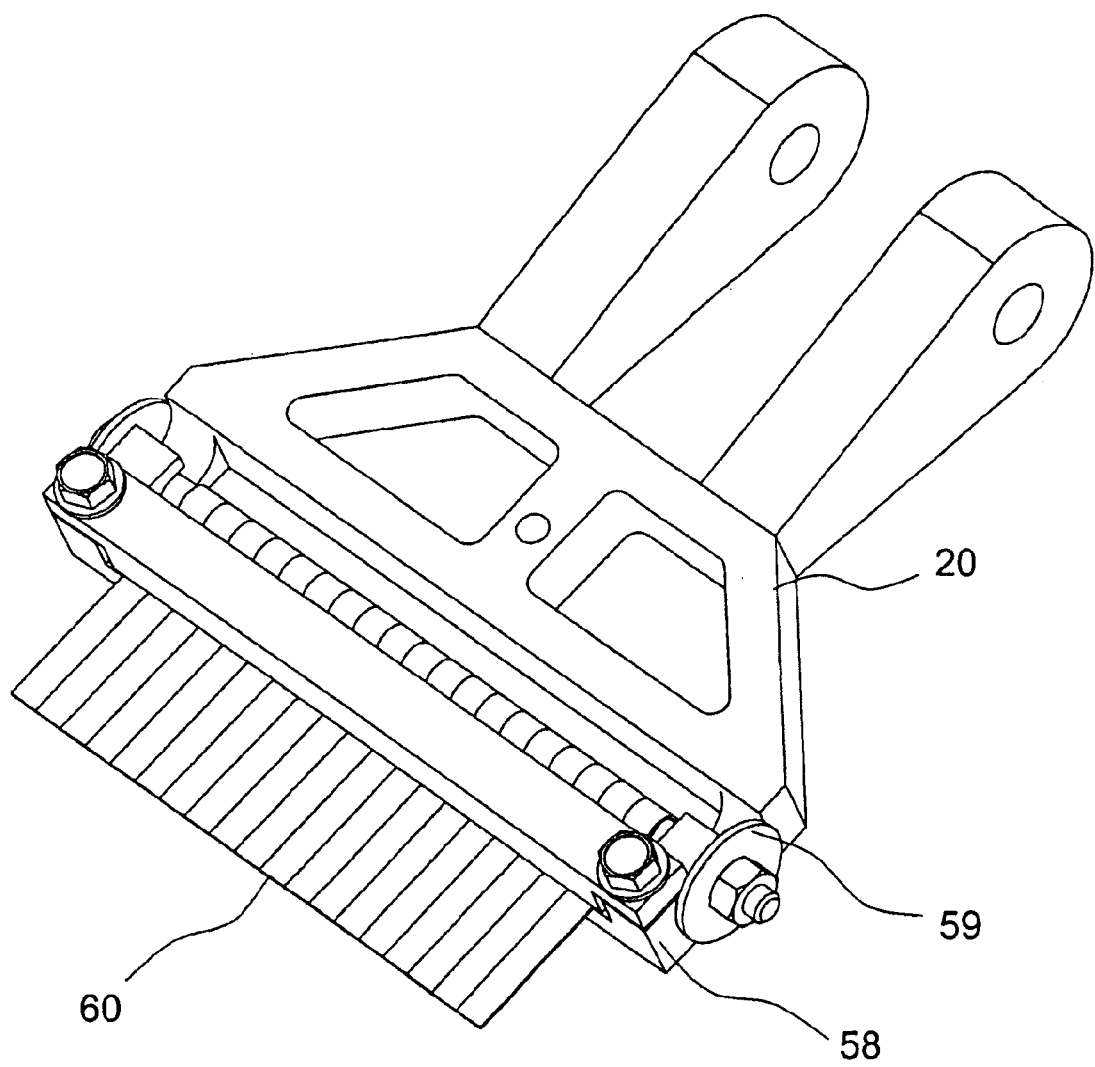
FIG. 7 depicts a pre-tensioning clamp attached to the load transfer plate of FIG. 1.

During a setup of the apparatus 10, the crosshead 81 and crosshead 92 are rigidly connected to a testing machine by the pins 72 and 90. An exposed section of the specimen 60 is rigidly secured by the clamps of the load transfer plates 20, 22, 24 and 26. For tensile loading of the specimen 60 and preferable if the specimen is a planar solid, the first wedge 52 attached to the load transfer plate 20 of FIG. 4 is used to secure the specimen. For compressive loading of the specimen 60, the second wedge 54 attached to the load transfer plate 20 of FIG. 5 is used to secure the specimen. For loading of fabric or other bendable material as the specimen 60, the tongue and groove clamp 56 attached to the load transfer plate 20 of FIG. 6 is used to secure the specimen. Alternatively, for loading of the specimen 60, the clamp 58 with the pre-tensioning roller 59 and attached to the load transfer plate 20 of FIG. 7 is used to secure the specimen. By a series of fasteners or by other fastening means known to those skilled in the art, wedges 52 and 56 as well as clamps 56 and 58 can be rigidly attached to the individual load transfer plates 20, 22, 24 and 26.

Figure 8:
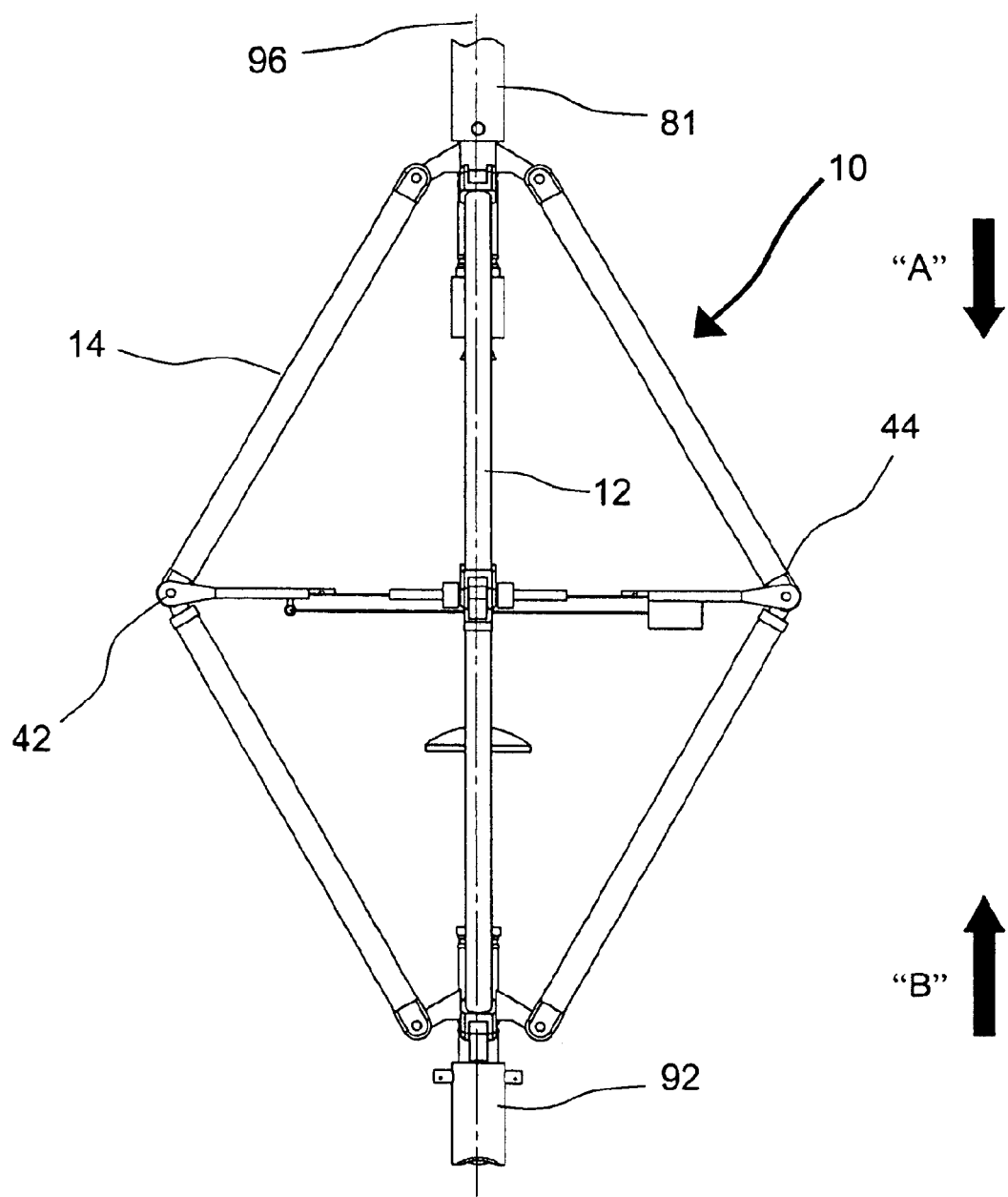
FIG. 8 depicts a side view of the apparatus of the present invention.

During a test and depicted by the configuration of the assembly 10 in FIG. 8, the downward or compressive movement in direction "A" of the crosshead 81 causes lateral links 42, 44, 46 and 48 of the linkages 12 and 14 to move outward from a longitudinal axis 96 thereby increasing in distance from each other to the assembly configuration of FIG. 1. More specifically, a compressive force is transmitted from the crosshead 81 by the rigid and oblong members 30, 32, 36 and 38 to vary the rhombus shape defined by the linkages 12 and 14. By rotation of the members 30, 32, 36 and 38 on the lateral links 42, 44, 46 and 48, the linkages 12 and 14 move outward. The increase in distance by the linkages 12 and 14 reflects the conversion of the compressive load by the crosshead 81 into a biaxial tension in the specimen 60. By positioning the third four-bar linkage in the same direction "A", tri-axial tension on the specimen 60 can be accomplished by the load transfer plates of the third four-bar linkage.

Separately or combined with the movement of the crosshead 81, the upward or compressive movement in direction "B" of the crosshead 92 causes lateral links 42, 44, 46 and 48 of the linkages 12 and 14 to move outward from the longitudinal axis 96 thereby increasing in distance from each other to the assembly configuration of FIG. 1. The increase in distance by the linkages 12 and 14 reflects the conversion of the compressive load by the crosshead 92 into a biaxial tension in the specimen 60. Similarly, by positioning the third four-bar linkage in the same direction "B", tri-axial tension on the specimen 60 can be accomplished by the load transfer plates of the third four-bar linkage.

Conversely, the upward or tensile movement of the crosshead B1 in direction "C" in FIG. 1 causes the lateral links 42, 44, 46 and 48 of the linkages 12 and 14 to move toward the axis 96 thereby decreasing a distance from each other. More specifically, a separating force similar to a tensile movement is transmitted from the crosshead 81 by the rigid members 30, 32, 36 and 38 to vary the rhombus shape defined by the linkages 12 and 14. By rotation of the members 30, 32, 36 and 38 on lateral links 42, 44, 46 and 48, the linkages 12 and 14 move to the axis 96. The decrease in distance between the linkages 12 and 14 reflects the conversion of the tensile load by the crosshead 81 into a compressive biaxial load in the plane of the specimen 60. Similarly, by positioning the third four-bar linkage in the same direction "C", tri-axial compression on the specimen 60 can be accomplished by the load transfer plates of the third four-bar linkage.

Separately or combined with the movement of the crosshead 81, the downward or tensile movement of the crosshead 92 in direction "D" in FIG. 1 causes the lateral links 42, 44, 46 and 48 of the linkages 12 and 14 to move toward the axis 96 thereby decreasing a distance from each other. The decrease in distance between the linkages 12 and 14 reflects the conversion of the tensile load by the crosshead 92 into a compressive biaxial load in the specimen 60. Similarly, by positioning the third four-bar linkage in the same direction "D", tri-axial compression on the specimen 60 can be accomplished by the load transfer plates of the third four-bar linkage.

Additionally, upon rotation of the crosshead 81 in direction "E", the first sleeve 62 of FIG. 2 rotates with respect to the second sleeve 64 thereby rotating the linkage 12 with respect to the linkage 14. This rotation thereby rotates the load transfer plates 24 and 26 of the linkage 12 with respect to the load transfer plates 20 and 22 of the linkage 14 such that an in-plane shear or torsional stress is applied to the specimen 60.

Separately, upon rotation of the crosshead 92 in direction "E", the first sleeve 82 rotates with respect to the second sleeve 84 thereby rotating the linkage 14 with respect to the linkage 12. This rotation thereby rotates the load transfer plates 20 and 22 of the linkage 14 with respect to the load transfer plates 24 and 26 of the linkage 12 such that an in-plane shear or torsional stress is applied to the specimen 60.

Figure 9:
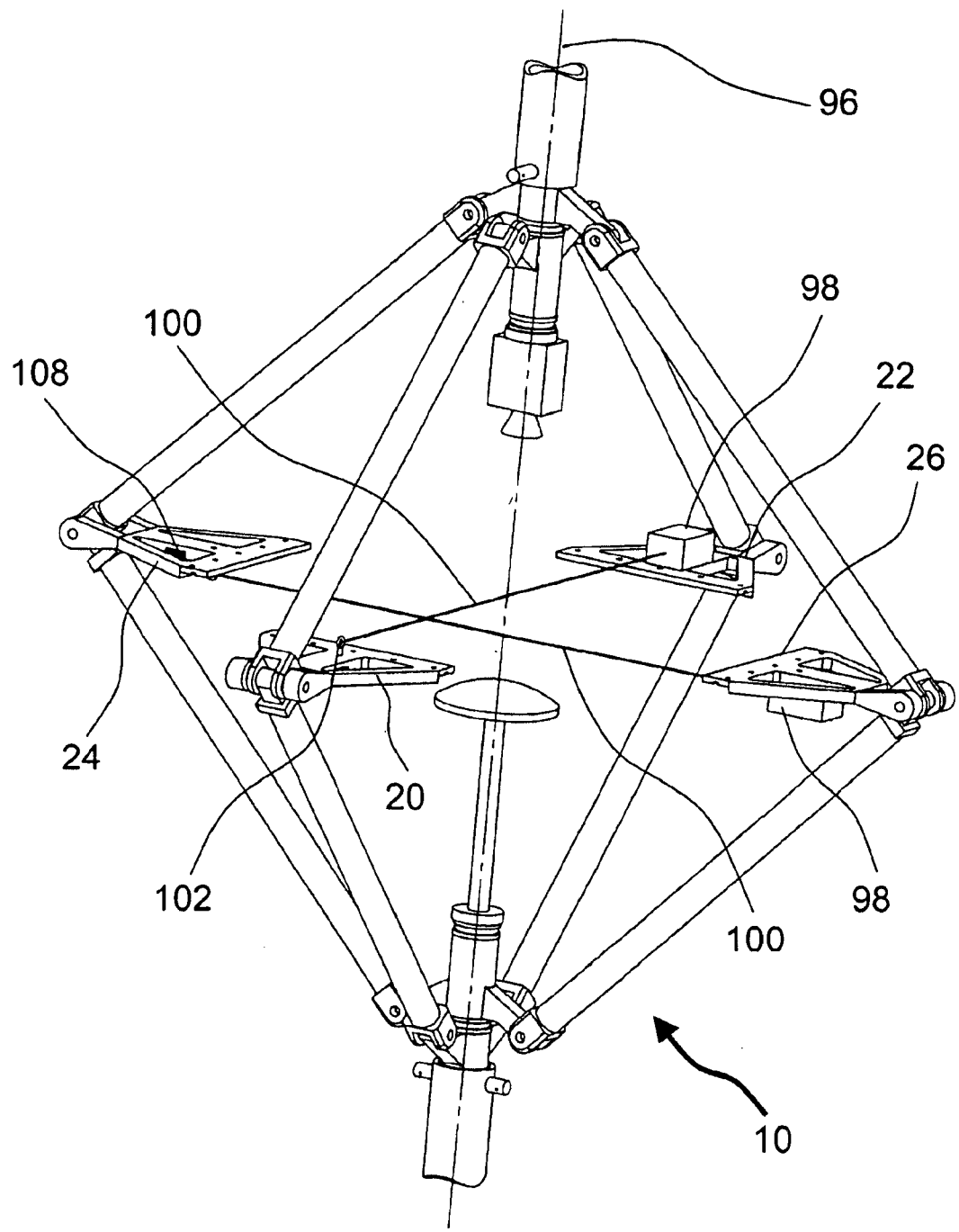
FIG. 9 depicts a perspective view of the multi-axial testing apparatus of the present invention detailing the measurement system for testing the specimen.

During any of the testing described above, the measurement system 28, typical of measurement systems known to those skilled in the art, measures the multi-axial displacements due to compression or tensile loading of the specimen. The measurement system 28 includes a conventional displacement wire transducer 98 placed on the load transfer plate 22. By a connecting wire 100, the transducer 98 is rigidly attached to a hook 102 on the load transfer plate 20 parallel to one transverse axis 104 of the biaxial loading. For a second transverse axis 106 of the biaxial loading, a separate transducer 98 and a separate connecting wire 100 (shown in FIG. 9) are positioned on the bottom surface of the load transfer plates 24 and 26. For a third transverse axis of a triaxial loading, a separate transducer and a separate connecting wire (not shown) may be on an alternate plane from the connecting wires 100 for the axis 104 and 106 in order not to interfere with either. Strain gauges 108 are placed on the sidewalls of the load transfer plates 20, 24 and on (but not shown) load-transfer plates 22, 26 to directly monitor the loading of the specimen 60.

To visually record the deformation of the specimen 60, a camera or another optical recording device 110 may be affixed to the second sleeve 64 of the joint assembly 16. Another feature would be the affixing of a puncturing or the shown draping mechanism 112 to the second sleeve 84 of the joint assembly 18 to conduct puncture and/or drape tests on the specimen 60.

As shown and described above, the specimen 60 is subject to an equal biaxial loading wherein the length of the load transfer plates 20, 22, 24 and 26 are equal. In a first variant of the embodiment of the present invention, an unequal biaxial loading of the specimen 60 is capable. To have an unequal biaxial loading ratio, the length of the load transfer plates 20 and 22 of the linkage 14 would differ from those of the load transfer plates 24 and 26 of the linkage 12. The displacement relationship caused by the unequal biaxial loading can easily be extracted by using the Pythagorean theorem.

Figure 10:
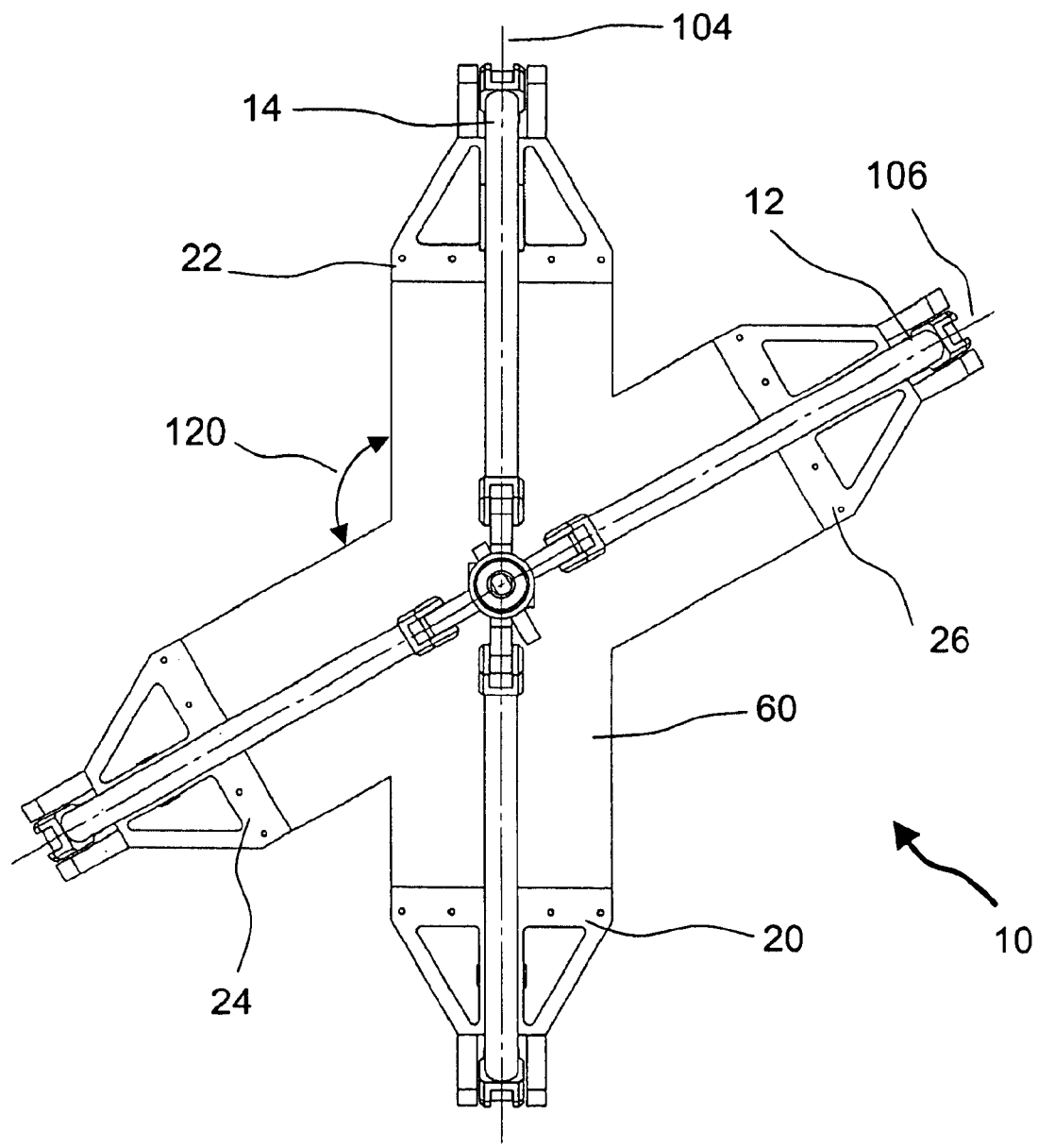
FIG. 10 depicts a top view of the apparatus of the present invention with the view taken from reference line 10—10 of FIG. 1 in which the specimen is positioned for non-orthogonal loading of the test specimen by varying the angle between the vertices of the linkages.

In a second variant of the embodiment of the present invention, the apparatus 10 is also capable of non-orthogonal (oblique) multi-axial loading of the specimen 60. Non-orthogonal multi-axial loading is particularly important for testing of braided or knitted fabrics and other non-orthogonal composite materials. As depicted in FIG. 10 for a test, the angle 120 between the axis's 104 and 106 of the linkages 12 and 14 can be varied by rotating either linkage to match an angle defined by non-orthogonal fiber directions.

As is obvious in view of the prior description of the movements of the apparatus 10, the apparatus is capable of loading the specimen 60 for uniaxial tension, uniaxial compression, biaxial tension, biaxial compression, in-plane shear, biaxial tension with in-plane shear, biaxial compression with in-plane shear and unequal biaxial compression with in-plane shear as well as any other loading and resultant testing derivable by those skilled in the art.

Thus by the present invention its objects and advantages 4 are realized and although preferred embodiments have been disclosed and described in detail herein, its scope should be determined by that of the appended claims.

What is claimed is:

1. An apparatus for testing the material properties of a specimen, said apparatus comprising:

a top joint assembly movable along a longitudinal axis of said apparatus, said top joint assembly having a first sleeve capable of rotation about the longitudinal axis with said first sleeve having at least two arms extending radially outward and longitudinally to a first end of said first sleeve, and said top joint assembly having a second sleeve adjacent to the first end of said first sleeve, said second sleeve having at least two arms extending radially outward and longitudinally to the first end of said first sleeve;

a bottom joint assembly including a first sleeve having at least two arms extending radially outward and longitudinally to a first end of said first sleeve of said bottom joint assembly and having a second sleeve adjacent to the first end, said second sleeve having at least two arms extending radially outward and longitudinally to the first end of said first sleeve of said bottom joint assembly;

a first linkage for enclosing the specimen, said first linkage having a first, second, third and fourth oblong bars, a first link between said first and second bars and a second link between said third and fourth bars wherein said first bar links to one arm of said first sleeve of said top joint assembly and said third bar links to another arm of said first sleeve of said top joint assembly and wherein said second bar links to one arm of said second sleeve of said bottom joint assembly and said fourth bar links to another arm of said second sleeve of said bottom joint assembly;

a second linkage for enclosing the specimen, said second linkage having a first, second, third, and fourth oblong bars, a link between said first and second bars and a second link between said third and fourth bars wherein said first bar links to one arm of said second sleeve of said top joint assembly and said third bar links to another arm of said second sleeve of said top joint assembly and wherein said second bar links to one arm of said first sleeve of said bottom joint assembly and said fourth bar links to another arm of said first sleeve of said bottom joint assembly; and a plurality of load transfer plates, each of said load transfer plates mechanically attached at a first end to each of said links of said first and second linkages such that said load transfer plates enclose the specimen in opposing pairs and such that a second end of each of said load transfer plates is securable to the specimen;

wherein movement by said top joint assembly along the axis toward said bottom joint assembly causes each of said links of said first and second linkages to move outward from the axis and each other for applying a tension loading to the specimen by said plurality of load transfer plates;

wherein movement by said top joint assembly along the axis away from said bottom joint assembly causes each of said links of said first and second linkages to move inward to the longitudinal axis and each other for applying a compression loading to the specimen by said plurality of load transfer plates;

wherein rotation of said first sleeve of said top joint assembly about the axis causes the movement of said plurality of load transfer plates of said first linkage in reaction to the rotation of said first sleeve of said top joint assembly for applying a torsional loading to the specimen.

2. The apparatus in accordance with claim 1 wherein said bottom joint assembly is movable along the longitudinal axis of said apparatus wherein movement by said bottom joint assembly along the longitudinal axis toward said top joint assembly causes each of said links of said first and second linkages to move outward from the longitudinal axis and each other for applying a tension loading to the specimen by said plurality of load transfer plates and wherein movement by said bottom joint assembly along the axis away from said top joint assembly causes each of said links of said first and second linkages to move inward to the longitudinal axis and each other for applying a compression loading to the specimen by said plurality of load transfer plates.

3. The apparatus in accordance with claim 2 wherein said first sleeve of said bottom joint assembly is capable of rotation about the longitudinal axis wherein rotation of said first sleeve of said bottom joint assembly about the longitudinal axis causes the movement of said plurality of load transfer plates of said second linkage in reaction to the rotation of said first sleeve of said bottom joint assembly for applying a torsional loading to the specimen.

4. The apparatus in accordance with claim 3 said apparatus further comprising an optical recording device positioned adjacent to said second sleeve of said top joint assembly such that said optical recording device is capable of recording the deformation of the specimen during loading.

5. The apparatus in accordance with claim 4 said apparatus further comprising a draping mechanism affixed to said second sleeve of said bottom joint assembly such that said draping mechanism is capable of draping tests of the specimen during the tension loading of the specimen.

6. The apparatus in accordance with claim 4 said apparatus further comprising a puncturing mechanism affixed to said second sleeve of: said bottom joint assembly such that said puncturing mechanism is capable of puncture tests of the specimen.

7. The apparatus in accordance with claim 1 wherein said load transfer plates of said first linkage vary in length from said load transfer plates of said second linkage thereby allowing an unequal loading of the specimen during movement of said top joint assembly along the axis.

8. The apparatus in accordance with claim 2 wherein said load transfer plates of said first linkage vary in length from said load transfer plates of said second linkage thereby allowing an unequal loading of the specimen during movement of said joint assemblies along the axis.

9. The apparatus in accordance with claim 3 wherein said load transfer plates of said first linkage vary in length from said load transfer plates of said second linkage thereby allowing an unequal loading of the specimen during movement of said joint assemblies along the longitudinal axis.

10. The apparatus in accordance with claim 4 wherein said load transfer plates of said first linkage vary in length from said load transfer plates of said second linkage thereby allowing an unequal loading of the specimen during movement of said joint assemblies along the longitudinal axis.

11. The apparatus in accordance with claim 6 wherein said load transfer plates of said first linkage vary in length from said load transfer plates of said second linkage thereby allowing an unequal loading of the specimen during movement of said joint assemblies along the longitudinal axis.

12. The apparatus in accordance with claim 1 said apparatus further comprising:

a third linkage for enclosing the specimen, said third linkage having a first, second, third, and fourth oblong bars, a first link between said first and second bars and a second link between said third and fourth bars wherein said first bar links to a third arm of said second sleeve of said top joint assembly and said third bar links to a fourth arm of said second sleeve of said top joint assembly and wherein said second bar links to a third arm of said first sleeve of said bottom joint assembly and said fourth bar links to a fourth arm of said first sleeve of said bottom joint assembly with a pair of load transfer plates mechanically attached at a first end to each of said links of said third linkage such that said load transfer plates enclose the specimen in opposing pairs and such that a second end of each of said load transfer plates of said third linkage is securable to the specimen;

wherein movement by said top joint assembly along the axis to said bottom joint assembly causes each of said links of said third linkage to move outward from the longitudinal axis and each other for applying a tension loading to the specimen by said pair of load transfer plates of said third linkage; and wherein movement by said top joint assembly along the axis away from said bottom joint assembly causes each of said links of said third linkage to move inward to the longitudinal axis and each other for applying a compression loading to the specimen by said pair of load transfer plates of said third linkage.

13. The apparatus in accordance with claim 12 wherein said bottom joint assembly is movable along the longitudinal axis of said apparatus wherein movement by said bottom joint assembly along the longitudinal axis to said top joint assembly causes each of said links of said first, second and third linkages to move outward from the longitudinal axis and each other for applying a tension loading to the specimen and wherein movement by said bottom joint assembly along the longitudinal axis away from said top joint assembly causes each of said links of said first, second and third linkages to move inward to the longitudinal axis and each other for applying a compression loading to the specimen.

14. The apparatus in accordance with claim 13 wherein said first sleeve of said bottom joint assembly is capable of rotation about the longitudinal axis wherein rotation of said first sleeve of said bottom joint assembly about the longitudinal axis causes the movement of said plurality of load transfer plates of said second and third linkages in reaction to the rotation of said first sleeve of said bottom joint assembly for applying a torsional loading to the specimen.

15. The apparatus in accordance with claim 14 wherein said load transfer plates of said first linkage vary in length from said load transfer plates of said second and third linkages thereby allowing an unequal loading of the specimen during movement of said joint assemblies along the axis.

16. An apparatus for testing the material properties of a solid specimen, said apparatus comprising:

a means for securing the solid specimen;

a means for applying a bi-axial compressional and bi-axial tensile load to the solid specimen;

a means for applying a torsional load to the solid specimen; and a means for measuring said compressional and tensile load.

17. An apparatus for testing the material properties of a specimen, said apparatus comprising:

a means for securing the specimen;

a means for applying a compressional and tensile load to the specimen wherein said means for applying a compressional and tensile load includes means for applying said compressional and tensile load at sections of the specimen in which the sections are non-orthogonal to each other;

a means for applying a torsional load to the specimen; and a means for measuring said compressional and tensile load.

18. The apparatus in accordance with claim 17 said apparatus further comprising means for visually recording the deformation of the specimen during said compressional, tensile and torsional load applications.

19. The apparatus in accordance with claim 18 said apparatus further comprising means for drape testing the specimen.

20. The apparatus in accordance with claim 18 said apparatus further comprising means for puncture testing the specimen.

* * * * *